United States Patent [19] [11] 4,387,061
Suzuki et al. [45] Jun. 7, 1983

[54] PROCESS FOR PREPARING PHOSPHINIC ACID DERIVATIVES OF AMINOTHIO METHYLCARBAMATES

[75] Inventors: Tetsumi Suzuki, Isehara; Naoshi Imaki, Atsugi; Takemi Nakanome, Sagamihara, all of Japan

[73] Assignee: Mitsubishi Chemical Industries Ltd., Japan

[21] Appl. No.: 294,634

[22] Filed: Aug. 20, 1981

[30] Foreign Application Priority Data

Sep. 2, 1980 [JP] Japan ................................. 55-121656

[51] Int. Cl.$^3$ ................................................ C07F 9/24
[52] U.S. Cl. ...................................... 260/968; 260/937; 260/938; 260/944

[58] Field of Search ......................................... 260/968

[56] References Cited

U.S. PATENT DOCUMENTS 4,081,536  3/1978  Nelson ................................. 424/211
4,208,409  6/1980  Nelson ................................. 424/209

Primary Examiner—Anton H. Sutto
Attorney, Agent, or Firm—Kenway & Jenney

[57] ABSTRACT

This invention relates to an improved process for producing certain phosphinic acid derivatives of aminothio methyl carbamate by reacting N-(halothio)phosphinic acid amide and a carbamate compound in the presence of a cupric catalyst in high yields. These compounds are known to be useful as insecticides.

11 Claims, No Drawings

PROCESS FOR PREPARING PHOSPHINIC ACID DERIVATIVES OF AMINOTHIO METHYLCARBAMATES

SUMMARY OF THE INVENTION

This invention relates to a process for preparing substituted thio derivatives of methylcarbamate. More particularly, this invention provides an improved process for preparing phosphinic acid derivatives of aminothio methylcarbamates useful as pesticides. It has been known that phosphinic acid derivatives of aminothio methylcarbamate are useful as pesticides because these compounds have reduced phytotoxicity, reduced mammalian toxicity and longer residual effectiveness. Japanese kokai No. Sho 53-92827, published Aug. 29, 1978 and kokai No. Sho 54-115377, published Sept. 7, 1979 can be referred to for the status of the art. According to these publications, these compounds are prepared by the coupling reaction between N-(halothio)phosphinic acid amides and carbamate compounds in the presence of a cuprous chloride catalyst and an acid acceptor.

Cuprous chloride catalyst increases the reaction rate of the coupling reaction, compared with that of the non-catalyzed coupling reaction. However, cuprous chloride does not retard the undesirable side-reaction between said N-(halothio)phosphinic acid amides and the acid acceptor to a negligible rate. Furthermore, cuprous chloride undesirably promotes the disproportionation of the desired product of phosphinic acid derivatives of aminothio methylcarbamates.

An objective of this invention is to provide an improved process for preparing phosphinic acid derivatives of aminothio methylcarbamate.

Another objective of this invention is to provide the improved process for preparing N-[(phosphinothioyl)amino]thio-methylcarbamates with a high yield.

These objectives have been realized according to the process of this invention.

DETAILED DESCRIPTION OF THE INVENTION

This invention involves the process for preparing N-[(phosphinothioyl)amino]-thio-methylcarbamates of the formula (III)

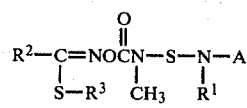

wherein A is of the formula (a) or (b)

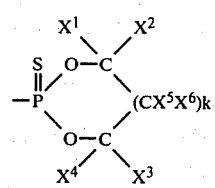

wherein $X^1$, $X^2$, $X^3$, $X^4$, $X^5$, and $X^6$ are the same or different and are selected from the group consisting of hydrogen, methyl and ethyl and k is 0 or 1;

wherein
$Y^1$ and $Y^2$ are the same or different and are lower alkoxy of 1 to 10 carbon atoms;
$R^1$ is a lower alkyl of 1 to 10 carbon atoms or cycloalkyl of 3 to 10 carbon atoms and $R^2$ and $R^3$ are lower alkyl of 1 to 10 carbon atoms;
which comprises reacting N-(halothio)phosphinic acid amide of the formula (I)

wherein $R^1$ and A have the same meanings as above; with a carbamate compound of the formula (II)

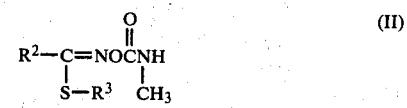

wherein $R^2$ and $R^3$ have the same meanings as above; in the presence of cupric bromide or cupric chloride and an acid acceptor.

One of the starting materials of the present invention is N-(halothio)phosphinic acid amide of the formula (I)

wherein $R^1$ is a lower alkyl group of 1 to 10 carbon atoms, preferably 1 to 4 carbon atoms. Specific examples of the alkyl group include methyl, ethyl, n-propyl, iso-propyl, n-butyl and t-butyl group. Also $R^1$ may be a cycloalkyl group of 3 to 10 carbon atoms, for example, cyclopropyl, cyclobutyl, cyclopentyl or cyclohexyl. Among these groups, propyl and t-butyl are most preferable.

wherein A is formula (a) or (b):

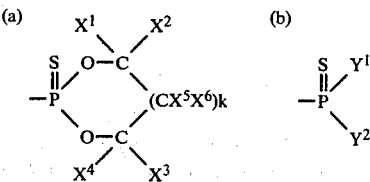 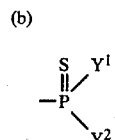

$X^1$, $X^2$, $X^3$, $X^4$, $X^5$ and $X^6$ are hydrogen, methyl or ethyl and k is 0 or 1. In the preferred compounds $X^1$, $X^2$, $X^3$ and $X^4$ are hydrogen and $X^5$ and $X^6$ are methyl groups.

$Y^1$ and $Y^2$ are generally lower alkoxy of 1 to 10 carbon atoms, for example, methoxy, ethoxy, n-propoxy, iso-propoxy, butoxy and octyloxy groups. Preferably, $Y^1$ and $Y^2$ are lower alkoxy of 1 to 4 carbon atoms and more preferably $Y^1$ and $Y^2$ are methoxy or ethoxy.

N-(halothio)phosphinic acid amides of the formula (I) are prepared in accordance with the known process shown by the following schema (1) and (2).

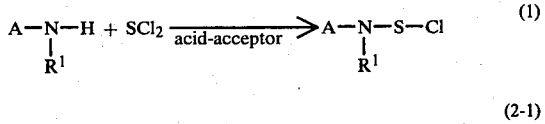

(1)

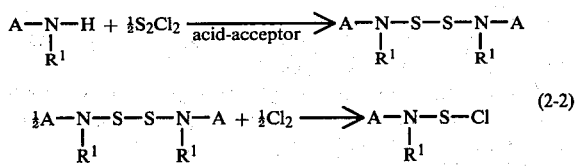

(2-1)

(2-2)

wherein $R^1$ and A are the same as above.

Since N-(halothio)phosphinic acid amides are generally unstable compounds, the reaction mixture obtained in accordance with the above schematic reaction (1) or (2) is directly subjected to the following step of the coupling reaction with carbamate compounds.

On the other hand, N-(halothio)phosphinic acid amide purified by recrystallization permits an increase the yield of the desired product.

The N-(halothio)phosphinic acid amides of the formula (I), include:
O,O-dimethyl N-(chlorothio)-n-propyl-phosphoramidothioate,
O,O-diethyl N-(chlorothio)-isopropylphosphoramidothioate,
O,O-diethyl N-(chlorothio)-n-butyl phosphoramidothioate,
2-[chlorothio(isopropyl)amino]-5,5-dimethyl-2-thioxa-1,3,2-phosphorinane,
2-[chlorothio(t-butyl)amino]-5,5-dimethyl-2-thioxa-1,3,2-phosphorinane,
2-[chlorothio(cyclohexyl)amino]-5,5-dimethyl-2-thioxa-1,3,2-phosphorinane,
2-[chlorothio(isopropyl)amino]-2-thioxa-1,3,2-phosphorinane
and
2-[chlorothio(cyclohexyl)amino]-2-thioxa-1,3,2-phosphorinane.

Another starting material in the present invention is a carbamate compound having the formula (II).

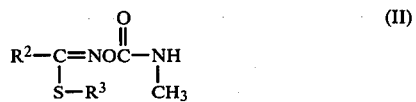

(II)

wherein $R^2$ and $R^3$ are lower alkyl of 1 to 10 carbon atoms such as methyl, ethyl, n-propyl, iso-propyl, n-butyl or t-butyl. Among those alkyls, lower alkyl of 1 to 4 carbon atoms are preferred and methyl is more preferred. These carbamate compounds can be prepared by the methods described in the prior art, for example, in the specification of Japanese publication No. 46-15498. In general, the carbamate compound may be used in an amount of 0.5-2 mole, preferably 0.8-1.2 mole per mole of N-(halothio)phosphinic acid amide.

When the carbamate is used in an amount more or less than the above ratio, an amount of one of the starting materials remains as an unreacted material which causes difficulty in the separation of the desired product from the reaction mixture. According to the present invention, it is necessary to use a cupric catalyst.

Useful catalysts are cupric halides selected from cupric chloride and cupric bromide. Cupric bromide is most preferable.

The amount of the cupric catalyst used in the present invention is usually within the range of 50 to 0.01% by weight, preferably of 10 to 0.1% per N-(halothio)phosphinic acid amide. It is disadvantageous to use the catalyst outside the above range.

At higher catalyst levels, the separation of the desired product may be difficult and at lower levels, the reaction velocity decreases.

According to the present invention, it is necessary to use an acid acceptor. Preferred acid acceptors are t-amines which include tri-lower alkyl amine such as trimethyl amine, trimethylamine, tri-n-butyl amine, and aromatic amines such as dimethylaniline and diethylaniline.

Among those amines, tri-lower alkyl amine is preferable and triethyl amine is most preferable.

Generally the amount of t-amine useful in the present invention varies within the range from 0.5 to 3 by mole ratio, preferably from 0.8 to 2 moles per mole of N-(halothio)phosphinic acid amide.

At lower levels of t-amine, the yield of desired product decreases disadvantageously.

Since these t-alkyl amines tend to react with N-(halothio)phosphinic acid amides to produce by-products, it is advantageous to conduct the reaction while adding the t-amine to the reaction mixture containing N-(halothio)phosphinic acid amide, carbamate compound and cupric catalyst.

Though the reaction temperature is not critical, the reaction is generally carried out at a temperature between about $-50°$ C. and $+50°$ C., preferably between about $-30°$ C. and $+20°$ C., more preferably between about $-25°$ C. and $0°$ C.

The reaction solvent is not critical so far as it is inert to the reaction. It is advantageous to use an organic solvent capable of dissolving the starting materials of N-(halothio)phosphinic acid amide and carbamate compound but immiscible in the desired product of substituted-thioderivatives of methylcarbamate.

Suitable solvents are, for example, diethylether, dibutylether, dimethoxyethan, diethoxyethan, tetrahydrofuran, dioxan, diglyme, triglyme, acetonitrile, dimethylformamide and dimethylsulfoxide.

Among those solvents, the preferred solvent is tetrahydrofuran, and it is helpful to treat the solvent, especially tetrahydrofuran, with molecular sieves to remove impurities and with a stabilizer prior to usage for the reaction.

When the reaction is carried out by using such organic solvent and cupric catalyst soluble in said organic solvent, the desired product of substituted-thioderivatives of methylcarbamate and t-amine hydrogen chloride are precipitated and isolated by filtration from the reaction medium containing cupric catalyst soluble in the organic solvent, unreacted starting materials and by-products.

The reactor to be used is not limited to any particular type but it is advantageous to use a reactor provided with an agitator such as a turbine winged with 4 paddles.

The pure desired product can be obtained by washing the precipitate above obtained, and if desired, the desired product can be purified by a conventional procedure, for example, by washing with an alkaline aqueous solution such as a saturated bicarbonate aqueous solution or an ammonium aqueous solution, recrystallization, active carbon treatment, chromatography, and like procedures.

According to the present invention using cupric halide as the catalyst and t-amine compounds as the acid acceptor, it is found that the reaction proceeds at a higher velocity to produce the desired product of substituted thioderivatives of methylcarbamate and the undesirable by-product forms at a reduced level. Therefore, the process of the present invention attains the desired product at a high yield and with a high selectivity.

The following examples describe the manner and process of making and using the invention and set for the best mode contemplated by the inventors of carrying out the invention but are not to be construed as limiting. In the following examples, all yields are by mole % against N-(halothio)phosphinic acid amide.

EXAMPLE 1

Methyl N-[[[[[(5,5-dimethyl-2-thioxo-1,3,2-dioxaphosphorinane-2-yl)t-butyl amino]thio]methylamino]carbonyl]oxy]ethanimidothioate.

A solution of 0.500 gm. (2.11 m mol) t-butylamino-5,5-dimethyl-2-thioxo-1,3,2-dioxaphosphorinane and 0.24 gm. (2.36 m mol) triethylamine in 2 ml tetrahydrofuran was added dropwise to 0.24 gm (2.36 m mol) sulfur dichloride in 3 ml tetrahydrofuran at a temperature between 0° C. and 5° C. with stirring under a nitrogen atmosphere and then the stirring was continued for 0.5 hrs. at 20° C.~25° C. Then, 0.035 gm. cupric bromide and 0.342 gm. (2.11 m mol) methyl N-[[(methyl amino)carbonyl]oxy]ethanimidothioate were dissolved in the above mixture thus obtained at 0° C. with stirring for 0.5 hrs.

After cooling the reaction temperature to −15° C., a solution of 0.32 gm. (3.17 m mol) triethylamine in 1 ml tetrahydrofuran was added dropwise to the above reaction mixture at −14° C.~−18° C. for 1 hr. Then the reaction temperature was increased gradually to 0° C. an interval of 1 hr. The reaction mixture was then diluted with 30 ml water to precipitate the products. The precipitated products were filtered and dried under reduced pressure. The white precipitate thus obtained weighed 0.876 gm. and the purity thereof is 87% by a liquid chromatography analysis. The yield is 84% (mole) against 2-t-butylamino-5,5-dimethyl-2-thioxo-1,3,2-dioxaphosphorinane and methyl N-[[(methyl amino)carbonyl]oxy]ethanimidothioate.

EXAMPLES 2–5

Following the same procedure as described in example 1, but employing a reaction temperature of −15° C.~0° C. instead 0° C.~5° C., the effects of various solvents and catalyst concentrations were examined. The results are shown as follows.

| Example | Catalyst | Amount of Cat.(1*) | Solvent | Yield (mole %) |
|---|---|---|---|---|
| 2 | CuBr$_2$ | 2.0 | THF | 64 |
| 3 | CuBr$_2$ | 10.8 | THF | 76 |
| 4 | CuBr$_2$ | 7.6 | CH$_3$O(CH$_2$)$_2$OCH$_3$ | 76 |
| 5 | CuBr$_2$ | 8.1 | CH$_3$CN | 70 |
| Comparative 1 | CuCl | 1.9 | THF | 62 |
| Comparative 2 | CuCl | 10.5 | THF | 63 |

Note:
THF: tetrahydrofuran
(1*)mole % against 2-t-butylamino-5,5-dimethyl-2-thioxo-1,3,2-dioxaphosphorinane

EXAMPLE 6

Methyl N-[[[[[(diethoxyphosphinothioyl)-isopropylamino]thio]methyl amino]carbonyl]oxy]ethanimidothioate O,O-diethyl isopropylphosphoramidothioate 0.502 gm. (2.38 m mol) and triethylamine 0.26 gm. (2.6 m mol) were dissolved in 4 ml of tetrahydrofuran under nitrogen atmosphere and the solution were cooled to 0° C. To the cooled solution, a solution of 0.27 gm. (2.6 m mol) of sulfur dichloride in 1 ml tetrahydrofuran were added dropwise at 0° C.~5° C. and the solution thus obtained were reacted at 20° C.~25° C. for 0.5 hr.

To the reaction mixture, 38 gm. of cupric bromide and 0.386 gm. (2.38 m mol) of N-[[(methylamino carbonyl]oxy]ethanimidothioate were added and the mixture was stirred at 0° C.~5° C. for 0.5 hr. Then, a solution of 0.36 gm. (3.57 m mol) of triethylamine in 1 ml tetrahydrofuran was added dropwise to the mixture obtained above at 0° C.~5° C. for an interval of 1 hr. Upon completion of the reaction, the reaction mixture was analyzed by liquid chromatography and gave a yield of 63% of the desired product.

EXAMPLE 7

Methyl N-[[[[[(5,5-dimethyl-2-thioxo-1,3,2-dioxaphosphorinane-2-yl)t-butylamino]thio]methylamino]carbonyl]oxy]ethanimidothioate 150 ml tetrahydrofuran, 35.60 gm. (0.15 mole) 2-t-butylamino-5,5-dimethyl-2-thioxo-1,3,2-dioxaphosphorinane and 18.21 gm. (0.18 mole) triethylamine are fed into 1 liter vol. of glass-reactor which is provided with an thermoregulator and a stirrer having a turbine winged with 4 paddles and 3 baffles therein.

All tetrahydrofuran used in the present examples 7 through 10 and comparative 3 was pretreated prior to usage with molecularsieves to remove water and peroxide. Also, said 2-t-butylamino-5,5-dimethyl-2-thioxo-1,3,2-dioxaphosphorinane was pre-purified by dissolving in methylene chloride and by washing with water.

To the contents of the reactor, maintained at −20° C.±2° C., a mixture of 18.53 gm. (0.18 mole) sulfur dichloride in 150 ml tetrahydrofuran was added dropwise over an interval of 1 hr. with stirring at 600 r.p.m. under nitrogen atmosphere and then the reaction was continued under the same conditions for 1 hr. Next, to the reaction mixture thus resulting, a mixture of 0.70 gm. cupric bromide and 24.33 gm. (0.15 mole) methyl N-[[(methylamino)carbonyl]oxy]ethanimidothioate in 150 ml tetrahydrofuran was added gradually for 10 minutes under the same conditions as above and 22.77 gm. (0.225 mole) triethylamine was added dropwise over an interval of 1 hr., followed by continuing the reaction for 2 hrs. under the same reaction condition.

After the reaction was completed, the reaction mixture thus obtained was analyzed by liquid chromatography to give the yields of desired product shown in the table 2.

EXAMPLES 8-10

Following the same procedure as described in Example 7, but changing the amount of the cupric bromide or the mole ratio of the starting materials, there was prepared methyl N-[[[[[(5,5-dimethyl-2-thioxo-1,3,2-dioxaphosphorinane-2-yl)t-butylamino]thio]methylamino]-carbonyl]oxy]ethanimidothioate.

The results are shown in table 2.

TABLE 2

| Example | Catalyst | Amount of Catalyst(*3) | MTM/NSPA(*2) (mole ratio) | Yield (%) |
|---|---|---|---|---|
| 7 | CuBr$_2$ | 7.0 | 1.0 | 89.3 |
| 8 | " | 4.0 | 1.0 | 87.4 |
| 9 | " | 4.0 | 1.2 | 90.7 |
| 10 | " | 2.0 | 1.2 | 89.5 |
| Comparative 3 | CuCl | 2.0 | 1.0 | 74.0 |

Note
(*2)MTM; methyl N—[[(methylamino)carbonyl]oxy] ethanimidothioate
NSPA; 2-t-butylamino-5,5-dimethyl-2-thioxo-1,3,2-dioxaphosphorinane
(*3)mole % against NSPA

COMPARATIVE 3

Following the same procedure as described in Example 7, but substituting cupric bromide for 0.30 gm. of cuprous chloride, there was produced the desired product. The yield is shown in Table 2.

What we claim:

1. A process for preparing N-thio-methylcarbamates of the formula (III):

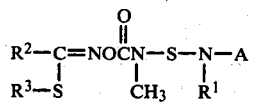 (III)

wherein A is of the formula (a) or (b):

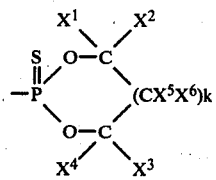 (a)

wherein X$^1$, X$^2$, X$^3$, X$^4$, X$^5$ and X$^6$ are the same or different and are selected from the group consisting of hydrogen, methyl and ethyl and k is 0 or 1;

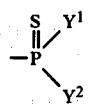 (b)

wherein
Y$^1$ and Y$^2$ are the same or different and are lower alkoxy of 1 to 10 carbon atoms;

R$^1$ is a lower alkyl of 1 to 10 carbon atoms or cycloaklkyl of 3 to 10 carbon atoms and R$^2$ and R$^3$ are lower alkyl of 1 to 10 carbon atoms, said process comprising:
reacting N-(halothio)phosphinic acid amide of the formula (I)

 (I)

wherein R and A are as defined above; with a carbamate compound of the formula (II):

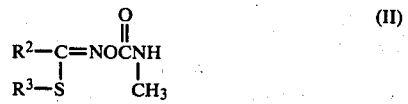 (II)

wherein R$^2$ and R$^3$ are as defined above; in the presence of an acid acceptor and a cupric halide selected from cupric bromide and cupric chloride.

2. The process according to claim 1, wherein cupric halide is cupric bromide.

3. The process according to claim 1 or 2, wherein cupric halide is used within the range of 50 to 0.01% by weight based on the weight of N-(halothio)phosphinic acid amide of the formula (I).

4. The process according to claim 3, wherein cupric halide is used within the range of 10 to 0.1% by weight based on the weight of N-(halothio)phosphinic acid amide of the formula (I).

5. The process according to claim 1, wherein the reaction is conducted at a temperature of from −30° C. to +20° C.

6. The process according to claim 5, wherein the reaction is conducted at a temperature of from −25° C. to 0° C.

7. The process according to claim 1, wherein the reaction is carried out by adding the t-amine acid acceptor to a reaction mixture containing N-(halothio)phosphinic acid amide of the formula (I), carbamate of the formula (II) and cupric halide.

8. The process according to claim 1, wherein the reaction is carried out by using carbamate of the formula (II) in an amount of 0.5 to 2 mole per mole of N-(halothio)phosphinic acid amide of the formula (I).

9. The process according to claim 8, wherein carbamate is used in an amount of 0.8 to 1.2 mole per mole of N-(halothio)phosphinic acid amide of the formula (I).

10. The process according to claim 1, wherein N-[(phosphinothioyl)amino]thio-methylcarbamate of the formula (III) is methyl N-[[[[[(5,5-dimethyl-2-thioxo-1,3,2-dioxaphosphorinane-2-yl)t-butyl amino]thio]methylamino]carbonyl]oxy]ethanimidothioate.

11. The process according to claim 1, wherein N-[(phosphinothioyl)amino]-thio-methylcarbamate of the formula (III) is methyl N-[[[[[(diethoxy phosphinothioyl)-isopropylamino]thio]methylamino]carbonyl]oxy]ethanimidothioate.

* * * * *